United States Patent [19]

Hardy et al.

[11] 4,260,625
[45] Apr. 7, 1981

[54] PENICILLINS

[75] Inventors: Kenneth D. Hardy, Horsham; George Burton, Carshalton Beeches, both of England

[73] Assignee: Beecham Group Limited, Great Britain

[21] Appl. No.: 101,488

[22] Filed: Dec. 10, 1979

[51] Int. Cl.³ .................. A61K 31/43; C07D 499/46
[52] U.S. Cl. .................................. 424/271; 260/239.1
[58] Field of Search ...................... 260/239.1; 424/271

[56] References Cited

U.S. PATENT DOCUMENTS

| 3,891,629 | 6/1975 | Diassi et al. | 260/239.1 |
| 4,035,359 | 7/1977 | Christensen et al. | 260/239.1 |
| 4,048,320 | 9/1977 | Clayton et al. | 260/239.1 |
| 4,053,609 | 10/1977 | Kawazu et al. | 260/239.1 |
| 4,092,309 | 5/1978 | Mich | 260/239.1 |
| 4,102,882 | 7/1978 | Firestone et al. | 260/239.1 |

Primary Examiner—Natalie Trousof
Assistant Examiner—Vera C. Clarke
Attorney, Agent, or Firm—Jacobs & Jacobs

[57] ABSTRACT

A class of penicillins with antibacterial activity having formula (I):

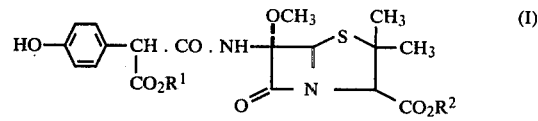

wherein $R^2$ is hydrogen or a pharmaceutically acceptable salting ion or in vivo hydrolyzable ester radical and $R^1$ is hydrogen, a pharmaceutically acceptable salting ion or a pharmaceutically acceptable ester forming radical.

13 Claims, No Drawings

PENICILLINS

This invention relates to a class of penicillins which have antibacterial activity and are of value in the treatment of infections in animals, including man and poultry, caused by a wide range of Gram-negative organisms.

In particular the invention relates to a class of 6-methoxy-α-carboxy penicillins. The invention also relates to a process for the preparation of such compounds, and to pharmaceutical compositions comprising them.

British Patent Specification No. 1,339,007 discloses inter alia a class of 6-substituted acylamino penicillins of general formula (A):

$$R_A-N\underset{\overset{\|}{O}}{\overset{H}{|}}\underset{}{\overset{R_B}{|}}\underset{N}{\underset{}{\bigg]}}\underset{CO_2R_C}{\overset{S}{\bigg\langle}}\underset{}{\overset{}{\bigg\rangle}} \quad (A)$$

where $R_A$ represents an acyl group, $R_B$ is a hydroxy or mercapto radical, a substituted or unsubstituted methoxy, ethoxy, methyl, ethyl, methylthio, or ethylthio radical, a carbamoyloxy, carbamoylthio, $C_{1-6}$ alkanoyloxy, $C_{1-6}$ alkanoylthio, cyano or carboxy radical or a derivative of a carboxy radical such as carbamoyl and $R_C$ is a hydrogen atom or a pharmaceutically acceptable esterifying radical or cation.

In that specification the only α-carboxy substituted acyl group $R_A$ which is specifically disclosed is 2-carboxyphenylacetamido and specific examples of such a side chain are exemplified with the following $R_B$ groups: methyl, cyano, aminomethyl and 2-carboxy-2-aminoethoxy. There is no disclosure of a 6-methoxy substituted penicillin having an α-carboxy-substituted acyl side chain.

In abstract No. 368 of the "Program and Abstracts" of the 14th Interscience conference on Antimicrobial Agents and Chemotherapy held on 11th—Sept. 13, 1974 in San Francisco, California, U.S.A., a report is made of a single 6-methoxy penicillin within formula (A) above, namely 6α-methoxy-6β-(2-carboxyphenylacetamido) penicillanic acid. That compound, although active against a number of Gram-negative organisms, is not effective against infections caused by pseudomonas organisms.

British Pat. No. 1,425,571 discloses certain esters of penicillanic acid derivatives having an organic acylamino side chain and an alkoxy substituent at the 6-position.

We have now found a small class of 6-methoxy-α-carboxy penicillins, which have activity against Gram-negative organisms including pseudomonas.

According to the present invention there is provided a compound of formula (I):

$$HO-\!\!\bigcirc\!\!-CH\underset{CO_2R^1}{|}\cdot CO\cdot NH-\!\!\!\underset{\overset{\|}{O}}{\overset{OCH_3}{|}}\!\!\overset{S}{\underset{N}{\bigg\langle}}\!\!\overset{CH_3}{\underset{CO_2R^2}{\bigg\rangle}}\!\!CH_3 \quad (I)$$

wherein $R^2$ is hydrogen or a pharmaceutically acceptable salting ion or in vivo hydrolysable ester radical and $R^1$ is hydrogen, a pharmaceutically acceptable salting ion or a pharmaceutically acceptable ester forming radical.

Suitable salting ions for the groups $R^1$ and $R^2$ include metal ions e.g. aluminium, alkali metal ions such as sodium or potassium, alkaline earth metal ions such as calcium or magnesium, and ammonium or substituted ammonium ions for example those from $C_{1-6}$ alkylamines, such as triethylamine, hydroxy-$C_{1-6}$ alkylamines such as 2-hydroxyethylamine, bis-(2-hydroxyethyl)-amine or tri-(2-hydroxyethyl)-amine, cycloalkylamines such as bicyclohexylamine, or from procaine, dibenzylamine, N,N-dibenzylethylenediamine, 1-ephenamine, N-ethylpiperidine, N-benzyl-β-phenethylamine, dehydroabiethylamine, N,N'-bis-dehydroabietyle-thylenediamine, or bases of the pyridine type such as pyridine, collidine or quinoline, or other amines which have been used to form salts with benzylpenicillin.

In vivo hydrolysable pharmaceutically acceptable ester radicals for the groups $R^1$ and $R^2$ are those which hydrolyse in the human body to produce the parent acid. Suitable examples include acyloxyalkyl groups such as acetoxymethyl, pivaloyloxymethyl, α-acetoxyethyl, α-acetoxybenzyl or α-pivaloyloxyethyl groups; alkoxycarbonyl-oxyalkyl groups, such as ethoxycarbonyloxymethyl and α-ethoxycarbonyloxyethyl; and lactone, thiolactone and dithiolactone groups, which form ester groups of formula:

$$-CO.O.-\underset{\underset{X'-C=Y'}{|\;\;\;\;\;|}}{CH-Z'}$$

wherein X' and Y' are oxygen or sulphur and Z' is an ethylene group or a 1,2-phenylene group optionally substituted by $C_{1-6}$ alkoxy, halogen or nitro.

Preferred ester groups are the phthalidyl and 5,6-dimethoxyphthalidyl esters.

Any ester function at the α-position in the side chain in formula (I) is suitable, so that, the group $R^1$ may be an alkyl, cycloalkyl, alkenyl, alkynyl, aryl or heterocyclic group any of which may be substituted. Suitable such groups include:

(a) alkyl especially $C_{1-6}$ alkyl such as methyl, ethyl, n- and iso-propyl, n-, sec-, iso- and tert-butyl and pentyl;

(b) substituted $C_{1-6}$ alkyl wherein the substituent is at least one of: chloro, bromo, fluoro, nitro, carbo ($C_{1-6}$ alkoxy), $C_{1-6}$ alkanoyl, $C_{1-6}$ alkoxy, cyano, ($C_{1-6}$) alkylmercapto, ($C_{1-6}$)alkylsulphinyl, ($C_{1-6}$)alkylsulphonyl, 1-indanyl, 2-indanyl, furyl, pyridyl, 4-imidazolyl, phthalimido, azetidino, aziridino, pyrrolidino, piperidino, morpholino, thiomorpholino, N-($C_{1-6}$ alkyl)-piperazino, pyrrolo, imidazolo, 2-imidazolino, 2,5-dimethylpyrrolidino, 1,4,5,6-tetrahydropyrimidino, 4-methylpiperidino, 2,6-dimethylpiperidino, alkylamino, dialkylamino, alkanoylamino, alkylanilino, or substituted alkylanilino wherein the substituent is chloro, bromo, lower alkyl or lower alkoxy;

(c) cycloalkyl and ($C_{1-6}$ alkyl) substituted cycloalkyl having from 3 to 7 carbon atoms in the cycloalkyl moiety;

(d) [2,2-di(lower alkyl)-1,3-dioxolon-4-yl]methyl;

(e) alkenyl having up to 8 carbon atoms;

(f) alkynyl having up to 8 carbon atoms;

(g) aryl groups such as phenyl and substituted phenyl wherein the substituent is at least one of chloro, bromo, fluoro, $C_{1-6}$ alkyl, $C_{1-6}$ alkoxy, $C_{1-6}$ alkanoyl, carbo-($C_{1-6}$)alkoxy, nitro, or di($C_{1-6}$) alkyl amino; and groups of formula:

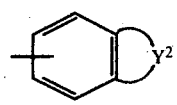

wherein $Y^2$ is
—CH=CH—CH=CH—
—CO—CH=CH—CO— or
—CO—CO—CH=CH—;
or

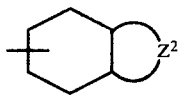

wherein $Z^2$ is $C_{1-6}$ alkylene such as $(CH_2)_3$—or—$(CH_2)_4$—, and substituted derivatives thereof wherein the substituent is methyl, chloro or bromo;

(h) aralkyl groups such as benzyl or substituted benzyl wherein the substituent is chloro, bromo, fluoro, $C_{1-6}$ alkyl, $C_{1-6}$ alkoxy, $C_{1-6}$ alkanoyl, carbo ($C_{1-6}$) alkoxy, nitro, or di($C_{1-6}$)alkylamino;

(i) heterocyclic groups such as: furyl, benzofuryl, benzothiophen, quinolyl, methyl-substituted quinolyl, phenazinyl, 1,3-benzodioxolyl, 3-(2-methyl-4-pyronyl), 3-(4-pyronyl) or methylpyridyl;

(j) other hydrocarbyl groups such as: ac - indanyl and substituted derivatives thereof wherein the substituent is methyl, chloro or bromo; ac - tetrahydronaphthyl and substituted derivatives thereof wherein the substituent is methyl, chloro or bromo; benzohydryl, trityl, cholesteryl, bicyclo[4.4.0]decyl.

Preferred groups for $R^1$ include $C_{1-6}$ alkyl, benzyl, phthalidyl, indanyl, phenyl, mono-, di-, and tri-($C_{1-6}$)alkyl substituted phenyl such as o-, m- or p-methylphenyl, ethylphenyl, n- or iso-propylphenyl, or n-, sec-, iso- or t-butylphenyl.

The compounds of formula (I) may be prepared by reacting a compound of formula (III) or an N-silyl or N-phosphorylated derivative thereof:

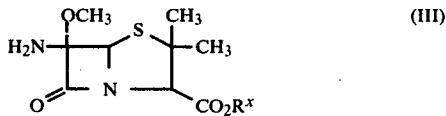

wherein $R^x$ is hydrogen or a carboxyl blocking group; with an N-acylating derivative of an acid of formula (IV):

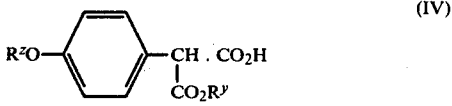

wherein $R^y$ is either a carboxyl blocking group or a group $R^1$ as defined with respect to formula (I) above, and $R^z$ is hydrogen or a hydroxyl blocking group, and thereafter if necessary carrying out one or more of the following steps:

(i) removal of any silyl or phosphoryl groups by hydrolysis or alcoholysis;

(ii) removal of any carboxyl or hydroxyl blocking groups;

(iii) converting the product to a salt or ester thereof.

By the term "N-silyl derivative" of compound (III), we mean the product of reaction of the 6-amino group of compound (III) with a silylating agent such as a halosilane or a silazane of the formula:

$L_3$ Si.U; $L_2$ Si.U$_2$; $L_3$ Si.NL$_2$;
$L_3$ Si.NH.Si $L_3$; $L_3$ Si.NH.COL; $L_3$ Si. NH.CO.NH.Si $L_3$;

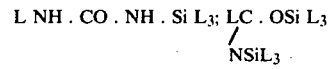

wherein U is a halogen and the various groups L which may be the same or different, each represents hydrogen or alkyl, alkoxy, aryl, or aralkyl. Preferred silylating agents are silyl chlorides, particularly trimethyl chlorosilane.

The term "N-phosphorylated" derivative of compound (III) is intended to include compounds wherein the 6-amino group of formula (III) is substituted with a group of formula:

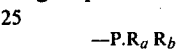

wherein $R_a$ is an alkyl, haloalkyl, aryl, aralkyl, alkoxy, haloalkoxy, aryloxy, aralkyloxy or dialkylamino group, $R_b$ is the same as $R_a$ or is halogen or $R_a$ and $R_b$ together form a ring.

Suitable carboxyl-blocking derivatives for the groups $CO_2R^x$ and $—CO_2R^y$ in formula (III) and (IV) include salts, ester, and anhydride derivatives of the carboxylic acid. The derivative is preferably one which may readily be cleaved at a later stage of the reaction. Suitable salts include tertiary amine salts, such as those with tri-$C_{1-6}$ alkylamines, N-ethyl-piperidine, 2,6-lutidine, pyridine, N-methylpyrrolidine, dimethylpiperazine. A preferred salt is with triethylamine.

Suitable ester groups of formula $CO_2R^x$ and $CO_2R^y$ include the following:

(i) —COOCR$_c$R$_d$R$_e$ wherein at least one of R$_c$, R$_d$ and R$_e$ is an electron-donor e.g. p-methoxyphenyl, 2,4,6-trimethylphenyl, 9-anthryl, methoxy, acetoxy, methoxymethyl, benzyl or fur-2-yl. The remaining R$_c$, R$_d$ and R$_e$ groups may be hydrogen or organic substituting groups. Suitable ester groups of this type include p-methoxybenzyloxycarbonyl, 2,4,6-trimethylbenzyloxy carbonyl, bis-(p-methoxyphenyl)methoxycarbonyl, 3,5-di-t-butyl-4-hydroxybenzyloxycarbonyl, methoxymethoxycarbonyl and benzyloxycarbonyl.

(ii) —COOCR$_c$R$_d$R$_e$ wherein at least one of R$_c$, R$_d$ and R$_e$ is an electron-attracting group e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining R$_c$, R$_d$ and R$_e$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) —COOCR$_c$R$_d$R$_e$ wherein at least two of R$_c$, R$_d$ and R$_e$ are hydrocarbon such as alkyl e.g. methyl or ethyl, or aryl e.g. phenyl and the remaining R$_c$, R$_d$ and R$_e$ group, if there is one, is hydrogen. Suitable esters of this type include t-butyloxycarbonyl, t-amyloxycarbonyl, diphenylmethoxycarbonyl and triphenylmethoxycarbonyl.

(iv) —COOR$_f$ wherein R$_f$ is adamantyl, 2-benzyloxyphenyl, 4-methylthiophenyl, tetrahydrofur-2-yl-tetrahydropyran-2-yl, pentachlorophenyl;

(v) Silyloxycarbonyl groups obtained by reaction of a silylating agent as described above with the carboxylic acid group;

(vi) CO$_2$P.R$_a$R$_b$, wherein R$_a$ and R$_b$ are as defined above.

The carboxyl group may be regenerated from any of the above esters by usual methods for example, acid- and base-catalysed hydrolysis, or by enzymically-catalysed hydrolysis. Alternative methods of cleavage include:

reaction with Lewis acids, such as trifluoroacetic acid, formic acid, hydrochloric acid in acetic acid, zinc bromide in benzene and aqueous solutions or suspensions of mercuric compounds. (The reaction with the Lewis acid may be facilitated by addition of a nucleophile such as anisole);

reduction with agents such as zinc/acetic acid, zinc/formic acid, zinc/C$_{1-6}$ alcohol, zinc/pyridine, palladised-charcoal and hydrogen, and sodium and liquid ammonia;

attack by nucleophiles, such as those containing a nucleophilic oxygen or sulphur atom for example alcohols, mercaptans and water; oxidative methods, for example, those which involve the use of hydrogen peroxide and acetic acid; and irradiation.

Suitable hydroxyl protecting groups R$^z$ include acyl groups such as acetyl and benzoyl, and aralkyl groups such as benzyl.

A reactive N-acylating derivative of the acid (IV) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be effected in the presence of an acid binding agent for example tertiary amine (such as triethylamine or dimethylaniline), an inorganic base (such as calcium carbonate or sodium bicarbonate) or an oxirane, which binds hydrogen halide liberated in the acylation reaction. The oxirane is preferably a (C$_{2-6}$)-1,2-alkylene oxide - such as ethylene oxide or propylene oxide. The acylation reaction using an acid halide may be carried out at a temperature in the range −50° to +50° C., preferably −20° to +30° C., in aqueous or non-aqueous media such as aqueous acetone, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (IV) or a salt thereof with a halogenating (e.g. chlorinating or brominating) agent such as phosphorus pentachloride, thionyl chloride or oxalyl chloride.

Alternatively, the N-acylating derivative of the acid (IV) may be a symmetrical or mixed anhydride. Suitable mixed anhydrides are alkoxyformic anhydrides, or anhydrides with, for example carbonic acid monoesters, trimethyl acetic acid, thioacetic acid, diphenylacetic acid, benzoic acid, phosphorus acids (such as phosphoric or phosphor acids), sulphuric acid or aliphatic or aromatic sulphonic acids (such as p-toluenesulphonic acid). The mixed or symmetrical anhydrides may be generated in situ. For example, a mixed anhydride may be generated using N-ethoxycarbonyl-2-ethoxy-1,2-dihydroquinoline. When a symmetrical anhydride is employed, the reaction may be carried out in the presence of 2,4-lutidine as catalyst.

Alternative N-acylating derivatives of acid (IV) are the acid azide, or activated esters such as esters with cyanomethanol, p-nitrophenol, 2,4-dinitrophenol, thiophenol, halophenol, including pentachlorophenol, monomethoxyphenol or 8-hydroxyquinoline; or amides such as N-acylsaccharins or N-acylphthalimides; or an alkylidene iminoester prepared by reaction of the acid (IV) with an oxime.

Some activated esters, for example the ester formed with 1-hydroxybenztriazole or N-hydroxysuccinimide, may be prepared in situ by the reaction of the acid with the appropriate hydroxy compound in the presence of a carbodiimide, preferably dicyclohexylcarbodiimide.

Other reactive N-acylating derivatives of the acid (IV) include the reactive intermediate formed by reaction in situ with a condensing agent such as a carbodiimide, for example N,N-diethyl-, dipropyl- or diisopropylcarbodiimide, N,N'-dicyclohexylcarbodiimide, or N-ethyl-N'-α-dimethylaminopropylcarbodiimide; a suitable carbonyl compound, for example N,N'-carbonyldiimidazole or N,N'-carbonylditriazole; an isoxazolinium salt, for example N-ethyl-5-phenylisoxazolinium-3-sulphonate or N-t-butyl-5-methylisoxazolinium perchlorate; or an N-alkoxycarbonyl-2-alkoxy-1,2-dihydroquinoline, such as N-ethoxycarbonyl-2-ethoxy-1,2-dihydroquinoline. Other condensing agents include Lewis acids (for example BBr$_3$—C$_6$H$_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan, or tetrahydrofuran.

The compounds (III) may be prepared for example by the method described by Jen et al (J. Org. Chem. 1973, 38, 2857) from an ester of a compound of formula:

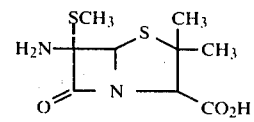

which compound may in turn be prepared from the corresponding 6-isocyano compound as described in our W. German Offenlegungsschrift No. 2,407,000.

Compounds of formula (I) may also be prepared by reacting a compound of formula (VI):

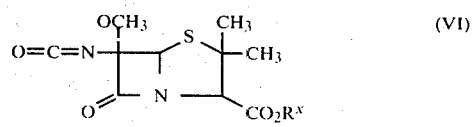

wherein R$^x$ is as defined above with respect to formula (III) above; with an acid of formula (IV) or a carbanion of formula (IV A):

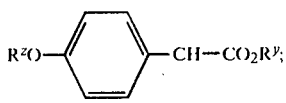

and thereafter if necessary carrying out one or more of the following steps:

(i) removal of any hydroxyl or carboxyl blocking group;

(ii) converting the product to a salt or ester thereof.

This reaction is preferably carried out at a temperature in the range $-10°$ to $+50°$ C. in an inert organic solvent, such as methylene dichloride, in the presence of a basic catalyst such as triethylamine, pyridine or a nitrogen containing aromatic mono- or bi-cyclic compound such as 4-methoxy(dimethylamino) pyridine, 1-methyl(benz)imidazole or imidazo[1,2-a] pyridine.

A third method of preparation of the compounds of formula (I) comprises:

(a) protecting the 3-carboxylic acid group of a 6-α-methoxy 6-β-acylaminopenicillanic acid with a carboxyl blocking group;

(b) reacting the protected penicillanic acid to form an imino bond on the 6-amido nitrogen atom;

(c) reacting the resulting compound to introduce a group $QR_f$ on the imino carbon atom, wherein Q is oxygen, sulphur or imino and $R_f$ is an alkyl group of from 1 to 12 carbon atoms or an aralkyl group of from 7 to 14 carbon atoms, to form an iminoether, iminothioether or amidine (when Q is O, S or N respectively);

(d) reacting with an acylating derivative of an acid of formula (IV) above;

(e) treating with water or an alcohol; and (f) thereafter if necessary carrying out one or more of the following steps:

(i) removal of any hydroxyl or carboxyl blocking groups;

(ii) converting the product to a salt or ester thereof.

In the above process, after protection of the 3-carboxylic acid group, the protected penicillanic acid is reacted with an agent to form an imino bond on the 6-amino nitrogen atom. Preferably an imino halide is formed of formula (VII):

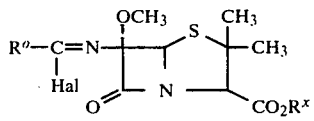

wherein R° is the residue of an organic acylamino sidechain of a penicillin, $R^x$ is a carboxyl blocking group and Hal represents a halogen atom. A suitable agent for preparing an imino halide is an acid halide in the presence of an acid binding agent such as a tertiary amine, e.g. pyridine, triethylamine, or N,N,-dimethylaniline. Examples of suitable acid halides are phosphorus pentachloride, phosgene, phosphorous pentabromide, phosphorus oxychloride, oxalyl chloride and p-toluene sulphonic acid chloride. Phosphorus pentachloride and phosphorus oxychloride are preferred. The reaction may be conducted under cooling, preferably at temperatures from 0° C. to $-30°$ C. when phosphorus pentachloride is employed. The amount of the tertiary amine is preferably 3-5 mols per mol of phosphorus pentachloride. It is also preferable to use the phosphorus halide in an amount slightly in excess of that of the starting material.

The resulting imino compounds are then treated to introduce a $-QR_f$ grouping, onto the imino carbon atom, to produce a compound of formula (VIII):

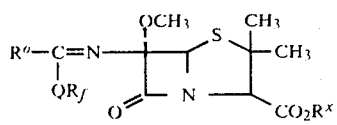

wherein R°, Q, $R_f$ and $R^x$ are as defined above with respect to formula (VII).

This is preferably effected by reacting an imino halide with a corresponding alcohol. Examples of suitable alcohols for reaction with the imino halide are aliphatic alcohols containing from 1 to 12 carbon atoms, preferably 1 to 5 carbon atoms, such as methanol, ethanol, propanol, isopropyl alcohol, amyl alcohol and butyl alcohol, and aralkyl alcohols such as benzyl alcohol and 2-phenyl-ethanol.

The reaction of the alcohol with the imino halide is preferably effected in the presence of an acid binding agent, such as a tertiary amine, preferably pyridine, and the reaction is usually carried out without isolating the imino halide from the reaction mixture.

Thereafter the compound (VIII) is caused to react with an N-acylating derivative of an acid of formula (IV). The comments made above concerning such N-acylating derivative, and the conditions for carrying out acylations also apply in this case. In particular the presence of a tertiary amine such as pyridine or N,N-dimethylaniline in the reaction system is preferred. The product from such an acylation has formula (IX):

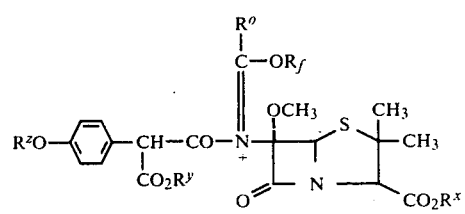

Finally, the addition compound (IX) is treated with water or alcohol. The water treatment may be conducted together with the isolation of the desired material. That is, water or a saturated aqueous solution of sodium chloride is added to the compound (IX) and then the aqueous layer formed is separated from the organic solvent layer.

Alternatively a compound of formula (IX A):

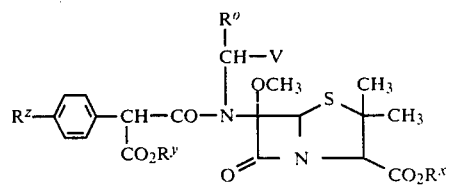

wherein R°, $R^x$, $R^y$ and $R^z$ are as defined with respect to formulae (IV) or (VII) and V is the residue of an N-acylating derivative of the acid (IV), (e.g. hydroxy, halogen, acyloxy, aryloxy, amino, cyano, azido); may be prepared by reaction of the corresponding N-acylating derivative of (IV) with the Schiff's base formed by reacting 6α-methoxy-6β-amino penicillanic acid (or a carboxyl protected derivative thereof) with an aldehyde R°.CHO. The compound (IXA) may be hydrolysed to a compound (I) with water optionally in the presence of acid or base.

A further method for the preparation of compounds of formula (I) is by hydrolysis of an 6-α-methoxy-N-acylbenzyl penicillin of formula (X):

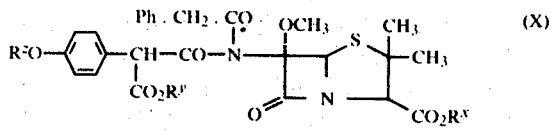

wherein $R^x$, $R^y$ and $R^z$ are as defined with respect to formulae (IV) or (VII). The hydrolysis may be an acid- or base-catalysed chemical hydrolysis or may be an enzymic hydrolysis with the aid of penicillin acylase. The compound (X) may be prepared either from an imino-halide compound of formula (VII) where R° is benzyl by reaction with a salt of the acid (IV); or by the action of an acid halide of the acid (IV) with a 6-N-alkali metal derivative of 6α-methoxy benzylpenicillin or with its 6-N-trimethylsilyl derivative.

The compounds of formula (I) wherein $R^1$ is an ester group may also be prepared by esterification of a compound of formula (XI) or a reactive esterifying derivative thereof:

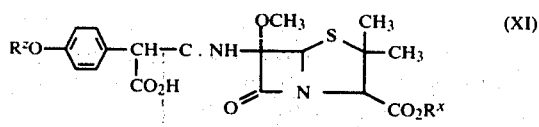

wherein $R^z$ and $R^x$ are as defined with respect to formulae (III) or (IV) with an esterifying derivative of an acid of formula $R^1OH$, wherein $R^1$ is as defined in formula (I) and thereafter if necessary carrying out one or more of the following steps:
(i) removal of any hydroxyl or carboxyl blocking groups;
(ii) converting the product to a salt or ester thereof.

Many methods of esterification using several different combinations of reactive esterifying derivatives are known from the literature. For example, the esterification reaction defined above may be achieved by reacting a compound of formula (XI A):

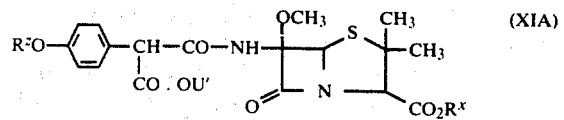

wherein $R^z$, $R^x$ are as defined with respect to formulae (III) or (IV) with a compound of formula (XII):

R¹—V'    (XII)

wherein $R^1$ is as defined in formula (I), under conditions which cause the elimination of the elements of compound U'V' with the consequent formation of an ester of formula (I); the symbols U' and V' in formula (XI A) and (XII) being such that either: U' represents hydrogen or a salt-forming ion and V' represents a hydroxy group, an alkylsulphonyloxy group, an arylsulphonyloxy group or a halogen atom; or U' represents an organic acyl group and V' represents a hydroxy group.

Usually it will be found satisfactory to react compound (XI A) wherein U' is a sodium or potassium ion; with compound (XII) wherein V' is a halogen atom, especially bromine or chlorine.

In the case where the group U' in reagent (XI A) is an organic acyl group, it will be clear that (XI A) is simply a mixed anhydride. The acyl group may be one of a wide variety of aliphatic or aromatic acyl groups but generally the alkoxy carbonyl groups (e.g. $C_2H_5OCO-$ group) are satisfactory.

Another reactive esterifying derivative of compound (XI) above is the acid halide, particularly the acid chloride. This compound may be reacted with the hydroxy compound $R^1OH$ in the presence of an acid binding agent to prepare the desired ester of this invention.

A further method for the preparation of compounds of formula (I) comprises reacting a compound of formula (XIII):

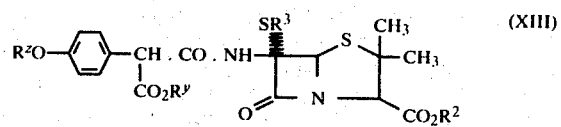

wherein $R^z$ and $R^y$ are as defined with respect to formulae (III) or (IV), $R^2$ is defined with respect to formula (I) and $R^3$ is lower alkyl or benzyl:
(A) with chlorine or bromine at −25° to −80° C. and subsequently decomposing the resultant halosulphonium halide with methanol and a base; or
(B) with methanol in the presence of a metal ion, such as a tellurium (III), lead (IV) bismuth (V) mercury, lead, cadmium or thallium salt.

Preferably this reaction is carried out at −50° to +25° C. in a solvent.

Compounds (I) may also be prepared by reducing a compound of formula (XV):

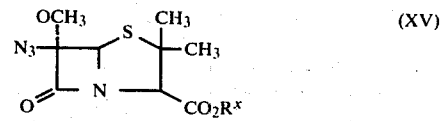

wherein $R^x$ is as defined with respect to formula (IV); and simultaneously or subsequently acylating with an N-acylating derivative of an acid of formula (IV) above and thereafter if necessary:
(i) removing any hydroxyl or carboxyl blocking group;
(ii) converting the product to a salt or ester thereof.

Suitable N-acylating derivatives of the acid (IV) are as described above.

Various methods of carrying out the reduction of the azido group may be used, but a preferred method is by catalytic hydrogenation using a noble metal catalyst such as platinum, palladium or oxides thereof.

The intermediate of formula (XV) may be prepared as described in British Pat. No. 1,339,007.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) above together with a pharmaceutical carrier or excipient.

The compositions may be formulated for administration by any route, although an oral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as dry product for reconstitution with water or other suitable vehicle before use. Such liquid preparations may contain conventional additives such as suspending agents, for example sorbitol, syrup, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired convention flavouring or colouring agents.

Suppositories will contain conventional suppository bases, e.g. cocoa butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene exide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration. Where the compositions comprise dosage units, each unit will preferably contain from 50–500 mg. of the active ingredient. The dosage as employed for adult human treatment will preferably range from 100 to 3000 mg. per day, for instance 1500 mg. per day, depending on the route and frequency of administration.

It will be clear that the side-chain of the penicillins of formula (I) contains a potentially asymmetric carbon atom. This invention includes all the possible epimers of compounds (I) as well as mixtures of them.

The following Examples illustrate the preparation of two of the compounds of this invention.

EXAMPLE 1

(a) Benzyl 6,α-methoxy-6,β-[D,L-2-benzyloxycarbonyl-2-(4-benzoxyphenyl)-acetamido]penicillinate Benzyl hydrogen 4-benzyloxyphenylmalonate (1.28 g) was stirred under reflux at 70° C. with thionyl chloride (5 ml) for 1½ hours. The solution was cooled and evaporated in vacuo. Toluene (5 ml) was added and the solution again evaporated in vacuo. Further toluene (5 ml) was added and the evaporation repeated to give the acid chloride.

Benzyl 6-β-amino-6-α-methylthiopenicillanate, p-toluene-sulphonate (1.57 gm) was shaken with ice-cold ethyl acetate (100 ml) and N/2 sodium bicarbonate solution (75 ml). The layers were separated and the organic phase washed with ice-cold water (2×75 ml), dried and evaporated in vacuo. The residue was dissolved in dry, distilled methanol (27 ml) and dry, distilled dimethylformamide (12 ml) added. The solution was cooled to −10° C. and treated with pyridine (0.57 ml). After further cooling to −20° C., mercuric chloride (0.813 gm) was added and the mixture stirred at −10° C. for 15 minutes. Dry diethyl ether (100 ml) was added and the solution filtered through Celite (Registered Trade Mark). After further dilution with dry diethyl ether (450 ml) the solution was washed with water (6×75 ml), dried and evaporated in vacuo. The resulting benzyl 6-β-amino-6-α-methoxy-penicillanate was dissolved in dry, alcohol-free methylene dichloride (40 ml) and pyridine (0.45 ml) added followed by the acid chloride in dry alcohol-free methylene dichloride (10 ml). The mixture was stirred at 0° to 5° C. for 2 hours. Water (20 ml) was added and the methylene dichloride evaporated in vacuo. The residue was shaken with ethyl acetate (75 ml) and water (55 ml) and the layers separated. The organic phase was washed with 10% citric acid (40 ml) N-sodium bicarbonate solution (40 ml), water (3×40 ml), dried and evaporated in vacuo to leave a yellow-brown gum.

The crude product was chromatographed on silica to give a 33% yield of purified material; t.l.c. (SiO$_2$:ethyl acetate/light petroleum b.p. 60°–80°; 1:2) Rf=0.28. N.M.R. (CDCl$_3$), δ=1.25 (6H, s, gem dimethyls), 3.38 (3H, d, —OCH$_3$), 4.52 (1H, s, 3H—), 4.78 (1H, s, >C$\underline{H}$—CONH—), 5.05 (2H, s, Ph—C$\underline{H}_2$—O—Ar), 5.22 (4H, s, —OC$_2$CH$_2$Ph), 5.70 (1H, s, 5-H), 7.00 (2H, d, Jab=9 Hz,

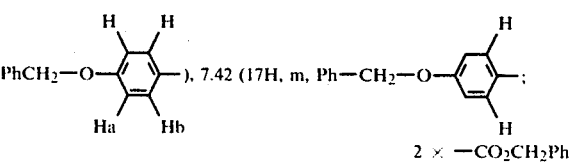

8.23 (1H, d, —CON$\underline{H}$).

(b)
6,α-Methoxy-6,β-[D,L-2-carboxy-2-(4-hydroxyphenyl)acetamido]penicillanic acid Benzyl 6,α-methoxy-6,β[D,L-2-benzyloxycarbonyl-2-(4'-benzyloxyphenyl)acetamido]penicillinate was dissolved in distilled ethanol (60 ml) and treated with water. Palladium on carbon 10% (0.40 gm) was added and the mixture hydrogenated for 1 hour. The mixture was filtered through Celite (Registered Trade Mark), the residue being washed with distilled ethanol (5 ml). Further catalyst (0.40 gm) was added and hydrogenation continued until removal of benzyl ester was complete as shown by T.L.c. on silica gel in Chloroform/acetone/acetic acid in 50:50:7. Water (25 ml) was added and the ethanol removed in vacuo. The mixture was made just alkaline with sodium bicarbonate solution, washed with diethyl ether and acidified with 5 N hydrochloric acid. Extraction with diethyl ether (2×10 ml), drying and evaporation in vacuo gave a mixture of 6,α-methoxy-6,β-[D,L-2-carboxy-2-(4-benzyloxyphenyl)acetamido]-penicillanic acid and the required 4-hydroxyphenyl product. The disodium salt of the two dicarboxylic acids was prepared by treating the mixture dissolved in dry acetone with two equivalents of sodium 2-ethylhexoate (as a 2 M solution in 4-methylpentan-2-one). The solid was filtered, washed with dry acetone and dried. This solid was dissolved in distilled water and hydrogenated as described above (omitting the use of ethanol at any stage), and the aqueous solution was acidified to pH 2.0 using dilute hydrochloric acid. The free acid thus formed was extracted into ethyl acetate, dried and evaporated in vacuo to give the title compound as its free di-acid; yield = 13%; t.l.c. (SiO$_2$: chloroform/acetone/acetic acid; 50:50:7) Rf = 0.16: N.M.R. [(CD$_3$)$_2$CO], δ = 1-2 (6H, m, gem dimethyls), 3.45 (3H, d, —OC$\underline{H}_3$) 4.45 (1H, s, 3-H), 4.85 (1H, s, Ph—C$\underline{H}$), 5.60 (1H, s, 5:H),

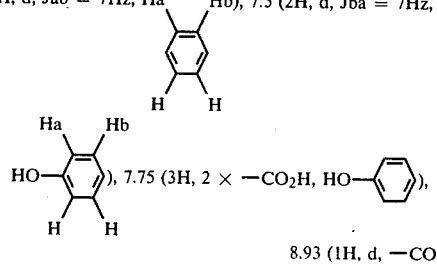

The acid was converted into its disodium salt as described above, yield = 98%; t.l.c. (SiO$_2$: chloroform/acetone/acetic acid—50:50:7) Rf = 0.18; ν$_{max}$ nujol (Registered Trade Mark) mull); 3200 (broad), 1765, 1670, 1609, 1255, 1105 cm$^{-1}$.

EXAMPLE 2

(a) Benzyl
6,α-methoxy-6,β-[D,L-2-phenoxycarbonyl-2-(4-benzyloxyphenyl)-acetamido]penicillinate Phenyl hydrogen 4-benzyloxyphenylmalonate (2.20 g) and DMF (2 drops) in dichloromethane (50 ml) were stirred at R.T. for two hours with oxyalyl chloride (0.45 ml) to give the acid chloride.

This acid chloride was used to acylate benzyl 6,β-amino-6-α-methoxy-penicillante (6 m mole) using the method described in Example 1(a) to give a 44.0% yield of purified product; t.l.c. (SiO$_2$; ethyl acetate/light petroleum b.p. 60°–80°, 1:1) Rf = 0.48; n.m.r. (CDCl$_3$) δ = 1.2–1.5 (6H, m, gem dimethyls), 3.47 and 3.49 (3H, 2×s, —OCH$_3$), 4.47 and 4.50 (1H, 2×s, 3H), 4.86 (1H, s, >C$\underline{H}$—CONH—), 5.15 (2H, s, —CH$_2$Ph), 5.27 (2H, s, —CH$_2$Ph), 5.66 (1H, s, 5H—), 6.9–7.8 (15H, m, aromatic protons and —CONH—).

(b)
6,α-Methoxy-6,β-[D,L,-2-phenoxycarbonyl-2-(4-hydroxy-phenyl)acetamido]-penicillanic acid Hydrogenolysis of the ester prepared above in the presence of 10% palladium or charcoal as described in Example 1 (b) gave the tital compound, t.l.c. (SiO$_2$: chloroform/acetone/acetic acid: 7:7:1) Rf = 0.41.

We claim:
1. A penicillin of formula:

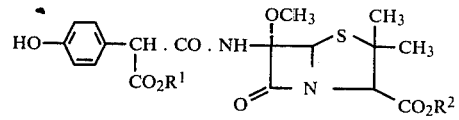

wherein R$^2$ is hydrogen or a pharmaceutically acceptable salting ion or in vivo hydrolysable ester radical; and R$^1$ is hydrogen, a pharmaceutically acceptable salting ion, or a pharmaceutically acceptable ester forming radical.

2. A penicillin as claimed in claim 1, wherein R$^1$ is hydrogen, a pharmaceutically acceptable salting ion or C$_{1-6}$ alkyl, benzyl, phthalidyl, indanyl, phenyl, or mono-, di-, or tri- (C$_{1-6}$)-alkyl substituted phenyl.

3. A penicillin as claimed in claim 2, wherein R$^1$ is hydrogen.

4. An epimer or epimeric mixture of a pencillin of claim 1.

5. 6,α-Methoxy-6,β-[D,L-2-carboxy-2-(4-hydroxyphenyl)acetamido]penicillanic acid or a pharmaceutically acceptable salt thereof.

6. An epimer or epimeric mixture of a penicillin of claim 5.

7. 6,α-Methoxy-6,β-[D,L-2-phenoxycarbonyl-2-(4-hydroxy-phenyl)-acetamido]-penicillanic acid or a pharmaceutically acceptable salt thereof.

8. An epimer or epimeric mixture of a penicillin of claim 7.

9. An antibacterial composition comprising an antibacterial amount of a compound of claim 1 and a pharmaceutically acceptable carrier or excipient.

10. An antibacterial composition comprising an antibacterial amount of a compound of claim 1 and a pharmaceutically acceptable carrier or excipient in oral or parenteral dosage form.

11. An antibacterial composition comprising an antibacterial amount of a compound of claim 1 and a pharmaceutically acceptable carrier or excipient wherein the antibacterial compound constitutes from 10 to 60% by weight of the composition.

12. A method of treating a bacterial infection in humans and animals which comprises administering to a human or animal in need thereof an antibacterially effective amount of a composition of claim 9.

13. A method according to claim 12 wherein the bacterial infection is caused by pseudomonas organisms.

* * * * *